(12) United States Patent
Murnick et al.

(10) Patent No.: US 11,525,804 B2
(45) Date of Patent: Dec. 13, 2022

(54) OPTOGALVANIC EFFECT DETECTION SYSTEM

(71) Applicant: Rutgers, The State University of New Jersey, New Brunswick, NJ (US)

(72) Inventors: Daniel E. Murnick, New Brunswick, NY (US); Mark DeGuzman, New Brunswick, NJ (US); Al Dutcher, New Brunswick, NJ (US); Orlando Hernandez, New Brunswick, NY (US)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 53 days.

(21) Appl. No.: 16/956,866

(22) PCT Filed: Dec. 21, 2018

(86) PCT No.: PCT/US2018/067169
§ 371 (c)(1),
(2) Date: Jun. 22, 2020

(87) PCT Pub. No.: WO2019/126687
PCT Pub. Date: Jun. 27, 2019

(65) Prior Publication Data
US 2021/0364468 A1 Nov. 25, 2021

Related U.S. Application Data

(60) Provisional application No. 62/609,083, filed on Dec. 21, 2017, provisional application No. 62/609,101, filed on Dec. 21, 2017.

(51) Int. Cl.
*G01N 27/66* (2006.01)
*G01N 33/00* (2006.01)

(52) U.S. Cl.
CPC ......... *G01N 27/66* (2013.01); *G01N 33/0027* (2013.01)

(58) Field of Classification Search
CPC . G01N 27/66; G01N 33/0027; G01N 21/1717
(Continued)

(56) References Cited

U.S. PATENT DOCUMENTS 5,706,082 A * 1/1998 Colgan ................ G01N 27/628
356/311
5,760,356 A * 6/1998 Garcia ................... H01H 13/06
200/302.1

(Continued)

FOREIGN PATENT DOCUMENTS

| CA | 22 01 241 C | 8/2000 |
|---|---|---|
| WO | WO 2015/114402 A2 | 8/2015 |

OTHER PUBLICATIONS

International Search Report and Written Opinion in corresponding PCT Application No. PCT/US2018/067169, dated May 1, 2019.
(Continued)

*Primary Examiner* — Christopher P McAndrew
(74) *Attorney, Agent, or Firm* — Leason Ellis LLP

(57) ABSTRACT

An optogalvanic effect (OGE) detection system utilizes an intracavity sample cell and a circuit that provides low noise stable excitation and maintenance of a radio frequency (rf) driven gas discharge within the sample cell and a direct current output proportional to the if driving voltage, associated monitoring devices and software. When an optical stimulus interacts with the discharge, any electrical change in the discharge can be simply determined with high precision and accuracy by measuring the impedance of the discharge via a measurement of the direct current output. In a preferred embodiment the rf gas discharge is created with a series resonant oscillator with two push pull sections connected together to generate the high voltage signal. A
(Continued)

current source provides a low noise stable current to power the oscillator sections. A band pass amplifier filters the current of the discharge prior to measuring it.

19 Claims, 8 Drawing Sheets

(58) Field of Classification Search
USPC .......................................................... 324/464
See application file for complete search history.

(56) References Cited

U.S. PATENT DOCUMENTS

| | | | |
|---|---|---|---|
| 5,818,580 A * | 10/1998 | Murnick | G01N 21/171 356/311 |
| 7,468,790 B2 * | 12/2008 | Sogan | G01N 21/68 438/9 |
| 7,616,305 B2 | 11/2009 | Murnick | |

OTHER PUBLICATIONS

International Preliminary Report on Patentability in corresponding PCT Application No. PCT/US2018/067169, dated Jul. 2, 2020.

* cited by examiner

OPTOGALVANIC EFFECT DETECTION SYSTEM

CROSS-REFERENCE TO RELATED PATENT APPLICATIONS

This application is a U.S. National Stage Application under 35 U.S.C. § 371 of International Patent Application No. PCT/US2018/067169, filed Dec. 21, 2018, and claims the benefit of priority under 35 U.S.C. Section 119(e) of U.S. Application Ser. No. 62/609,101, filed Dec. 21, 2017 and of U.S. Application Ser. No. 62/609,083, filed Dec. 21, 2017, all of which are incorporated herein by reference in their entireties. The International Application was published on Jun. 27, 2019 as International Publication No. WO 2019/126687 A1.

STATEMENT OF GOVERNMENT SUPPORT

This invention was made with government support under grant number 1434918 awarded by the National Science Foundation. The government has certain rights in the invention.

TECHNICAL FIELD

The present invention is generally directed to apparatus making use of the optogalvanic effect (OGE). i.e., the electrical response to an optical stimulus in gas discharges, in various instruments, such as laser-based isotope analyzers, trace element detectors and laser stabilization devices.

BACKGROUND OF THE INVENTION

The electrical response to an optical stimulus in gas discharges. i.e., the optogalvanic effect (OGE), has been known since 1928 when interactions were noted on adjacent neon discharges. It became important beginning in the 1960s when OGEs were observed in the development of gas discharge lasers and, especially in the 1970s, when OGE spectroscopy with tunable lasers became widespread. An extensive review of the subject to date was published in B. Barbieri, N. Beverini and A. Sasso, "Optogalvanic Spectroscopy," Rev Mod Phys, 62: 603-644. (1990). In 1994 the use of the OGE for isotope ratio analysis was reported, with several patents subsequently issued.

For isotope analysis work, low pressure rf discharges have been used. The rf oscillator circuit is coupled to the plasma by placing the sample inside the oscillator circuit. Such a discharge has useful properties. In particular, the absence of internal electrodes eliminates sputtering and contamination, and an rf discharge can be driven with high stability at lower pressure than possible with dc discharges. Working at lower pressures minimizes the pressure broadening required for high resolution. The impedance changes in the discharge induced by atomic or molecular transitions can be monitored with a good signal-to-noise ratio on the oscillator current if a regenerative oscillator, such as a Colpitts circuit, is used.

The isotope analysis work to date employed variations of a radio frequency oscillator circuit introduced by May and May, "Solid□state radio frequency oscillator for optogalvanic spectroscopy: Detection of nitric oxide using the 2□0 overtone transition," Rev. Sci. Instrum. 57, 2242 (1986). The discharge circuit should be stable, with low power and low electrical noise. Typically, one monitors the driving rf voltage amplitude variation to obtain an OGE signal waveform. For this type of oscillator, it is necessary to carefully frequency tune the rf circuit for best impedance matching, and also to minimize extraneous changes to the discharge due to temperature or pressure changes in order to obtain stable low noise-operation. Any mechanical perturbation can also cause an electrical response that may add random noise to the system. As discussed in B. Barbieri. N. Beverini and A. Sasso, "Optogalvanic Spectroscopy," Rev Mod Phys. 62: 603-644. (1990), poorly designed discharge circuitry can be limited by electrical noise as well as rf pickup and ground loop problems leading to poor experimental results. With this type of oscillator, a variation in rf amplitude is the output in response to slowly varying (fixed frequency chosen in the range of ~70 to 250 Hz) laser irradiation. The positive- and negative-going half cycles are peak rectified to produce a differential output.

SUMMARY OF THE INVENTION

In accordance with the present invention an OGE detection system is used for the detection of dilute species with unprecedented sensitivity.

In an illustrative embodiment the OGE system can detect especially rare gases such as $^{14}C$ in ambient $CO_2$ where the concentration is about 1 part per trillion. To detect $^{14}CO_2$ requires the use of two OGE systems, one for an unknown sample and a second for a stable reference system, where the reference is highly enriched in $^{14}C$- to a level near 1%.

The reference cell allows sensitivity to a few parts per thousand or about 1 part in $10^5$. The sample cell is placed inside a laser cavity where the higher laser power and vastly increased path length due to the stored (reflected) light, amplifies the OGE by ~ $10^7$, hence allowing detection at the part per trillion level. By carefully taking the ratio of the sample to the reference, and averaging for longer times (several minutes), accuracies of a few percent in the measured OGE are obtained. Using a series of reference samples, a calibration curve can be obtained thus allowing the measurement of unknown samples.

The system is used for determining the composition of an analyte which is placed in a sample cell and maintained in gaseous form in an electrical discharge. Radiation, e.g., a laser beam, is applied to the analyte in the discharge so that the radiation interacts with a first species in the analyte to produce an optogalvanic effect. i.e., a change in the discharge current. The electrical impedance of the discharge is monitored. e.g., by measuring the discharge current and an impedance signal representing the impedance.

While the radiation is impinging on the analyte the amplitude of the radiation is varied at a first modulation frequency. This causes the impedance signal to have a first component varying at a first component frequency equal to the first modulation frequency or a harmonic thereof. Then a circuit is used to detect the amplitude of the first component in order to provide a first value representing the amplitude of the first component, whereby the first value represents the amount of the first species in the analyte. The detecting step is performed so that the value is substantially independent of the phase of the first component relative to the phase of the periodic variation in amplitude of the first radiation. By having a reference cell a signal representing a fixed concentration of the analyte can be generated. The reference signal can then be used for laser stabilization and power normalization as well.

As a further process where applicable, a second radiation can be applied to the analyte in the discharge so that this second radiation interacts with a second species in the analyte to produce an optogalvanic effect. As with the first radiation, the second is periodically varied in amplitude at a second modulation frequency. This generates another impedance signal that includes a second component varying at a second component frequency equal to the second modulation frequency or a harmonic thereof. The circuit detects the amplitude of the second component to provide a second value representing the amplitude of the second component, whereby the second value represents an amount of a second species in the analyte. This second detecting step is performed so that the second value is substantially independent of the phase of the second component relative to the phase of the periodic variation in amplitude of the second radiation. The second component signals can be used for species normalization.

While the high voltage oscillator for controlling the discharges, the current supply for the oscillator and the hand pass amplifier may be any convenient circuit, in one embodiment of the present invention the oscillator of the OGE system includes 1) a stable low noise high voltage oscillator, 2) a low noise stable current source and 3) multiple feedback (MFB) band pass amplifiers. The OGE system functions better when it is utilized in an oscillator designed to achieve lower noise OGE signals and better stability.

The high voltage oscillator of the embodiment has left/right symmetry where the left side is a variation of a parallel resonant Pierce oscillator. At resonance, only resistance is left. Therefore, the current is in phase with the drive voltage. Further a 180° inversion is created, which in combination with the amplifier inversion produces non-inversion for total positive feedback or regenerative oscillation. The transistors operate in class D mode, so they do not generate noise.

The resistance of the resonance is reflected as the DC resistance of the oscillator at the power supply rail and can be used to monitor the OGE. When used with a current source supply, DC resistance changes will produce supply voltage changes. Thus, the oscillator of this embodiment is self-demodulating, i.e., the feedback stabilizes the frequency.

The oscillator requires a low noise current source to allow for the detection of small load changes. The current power source uses a low band pass filter with a cutoff of ~5 Hz, greatly reducing the op amp noise contribution. By means of negative feedback a constant current supply is provide to the oscillator.

The demodulated load changing supply voltage is fed to the base band amplifier, which has two stages that are multiple feedback (MFB) band pass amplifiers. They provide significant gain and band limiting to provide a signal suitable for acquisition.

BRIEF DESCRIPTION OF THE DRAWINGS

The foregoing and other objects and advantages of the present invention will become more apparent when considered in connection with the following detailed description and appended drawings in which like designations denote like elements in the various views, and wherein.

DETAILED DESCRIPTION OF THE INVENTION

Figure 1:
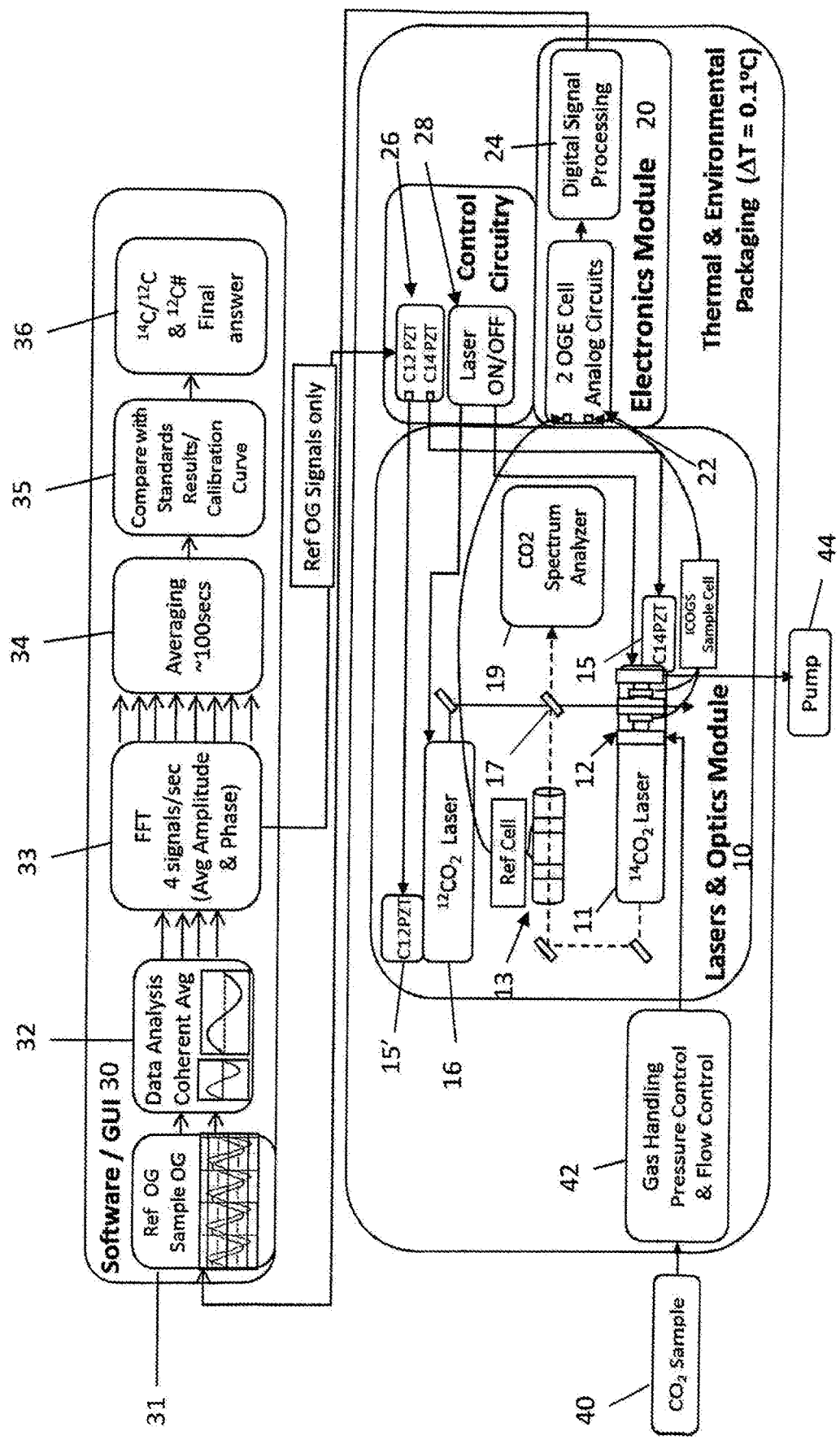
FIG. 1 is a block diagram of the optogalvanic effect detection system of the present invention.
Figure 8:
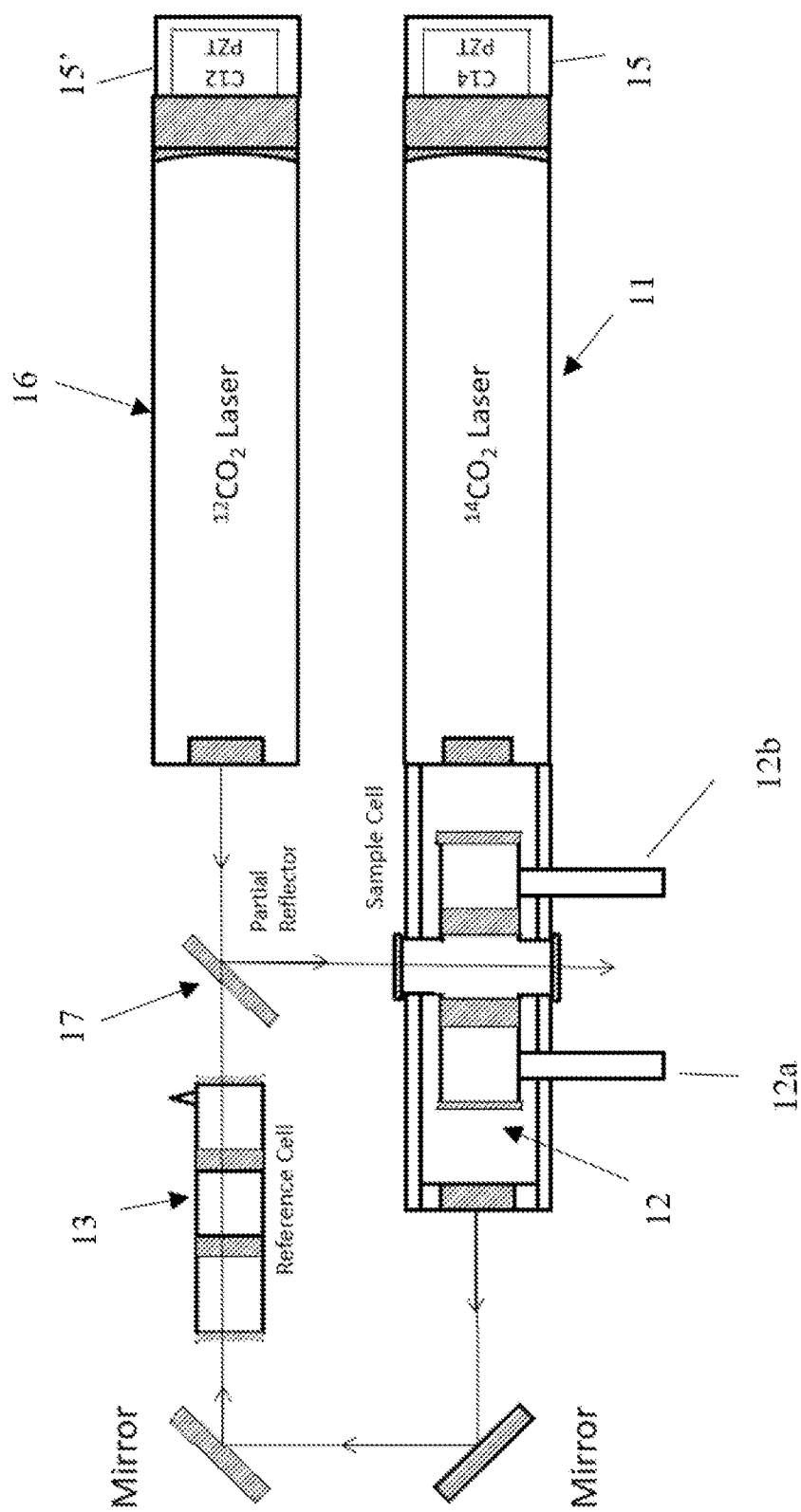
FIG. 8 is a schematic illustration of the optical arrangement of FIG. 1 showing the sample cell inside a laser cavity.

A system for unprecedented sensitivity for OGE detection of dilute species is shown in FIG. 1. The heart of the system is the lasers and optics module 10 containing a narrow band $^{14}CO_2$ laser 11, capable of wavelength tuning and stabilization, with an intracavity OGE sample cell 12. The system can use a gas laser that is either excited by high voltage DC or an alternating radio frequency (rf) source. Analogous configurations can be used with solid state lasers. The laser 11, 16 employed can be tuned to a specific laser line by the use of a diffraction grating and/or a PZT controlled mirror 15, 15' to vary the cavity length. A far infrared grating spectrometer 19 or other course wavelength monitor is useful for confirmation of specific wavelengths. The range of possible laser lines is determined by the details of the specific laser, such as temperature, gas composition and output coupler. Laser lines with wavelengths longer than 11.7 microns (P(20) to P(24) for $^{14}CO_2$) are expected to have the highest sensitivity for $^{14}CO_2$ detection based on optimization of the resonant OGE component to the off resonant background components from other $CO_2$ isotopes. An important feature is that a sample cell 12, which is exposed to high frequency discharge, is located in the cavity of laser 11. See FIG. 8. Also important is the stabilized $^{12}CO_2$ laser 16 for determining $^{12}CO_2$ content in the sample via a single pass OGE shown in the FIGS. 1 and 8 via the transverse ports in the sample cell 12.

Another significant component is an external reference cell 13, which is also subject to high frequency discharge, contains $CO_2$ enriched in $^{14}CO_2$ to a level that can easily be detected with a single pass of the extracted laser beam of laser 11. The external reference cell 13 serves to provide signals for stabilizing the power and wavelengths of both the $^{12}CO_2$ and $_{14}CO_2$ lasers 11, 16 and for monitoring laser fluctuations. A second important function of the reference cell 13 is to monitor the stability of the system. The ratio of $^{12}CO_2$ OGE signals from the sample and reference cells should be constant and proportional to the $^{12}CO_2$ concentration ratios in the two cells. The similar ratio for the $^{14}CO_2$ signals should also be constant but is not proportional to their corresponding $^{14}CO_2$ concentration ratios due to background effects.

Identical excitation and detection circuits, discussed above and shown in the control circuitry/electronics module 20 are used to energize both the sample cell 12 and reference cell 13. It is best to minimize extraneous changes to the discharge due to temperature or pressure changes in order to obtain stable low noise-operation. Any mechanical perturbation can also cause an electrical response that may add random noise to the system. The reference cell response is a critical diagnostic for obtaining quality data. An unstabilized $CO_2$ laser can drift several hundred megahertz around the center of the $^{14}CO_2$ resonance laser line; whereas a stabilized laser can be locked to within a kHz of the line center. See, C. Freed, "$CO_2$ Isotope Lasers and Their Applications in Tunable Laser Spectroscopy," *Tunable Lasers*

Handbook. Optics and Photonics. 1995. Pages 63-165, Academic Press The Doppler broadened resonance line width in a low power OGE discharge is about 40 MHz, so that stabilization to within a few MHz of line center is required for quality operation.

As shown in FIG. 1, the laser frequencies are picked up in the signals sent to the analog circuits in electronics module 20. These are processed in circuit 24 and the software GUI 30. The software and graphical user interface module 30 allows automated experimental control and analysis via the control circuitry shown in FIG. 1. The two lasers are electronically modulated at incommensurable frequencies; typically, one lower than 100 Hz for $^{14}C$ and one above 100 Hz for $^{12}C$, and separation of $^{12}CO_2$ and $^{14}CO_2$ signals is achieved by coherent averaging in module 32 followed by Fourier analysis in module 33. Circuit 33 feeds the laser frequency signals back to control circuits 26, which can be a section of a National Instruments Model 6356 Series Data Acquisition circuit. The lasers are stabilized via PID algorithms executed in circuit 26 that apply correction voltages to the PZT transducers 15, 15' to move the laser cavity mirrors to change the laser frequencies so as to compensate for any frequency shift due to thermal variations. Temperatures are also monitored in the laser and cell regions, and pressure and flow are monitored and controlled in the sample cell.

In operation a $CO_2$ sample 40 is delivered to gas handling, pressure control and flow control module 42. This module 42 delivers the sample 40 to the gas input 12a of sample cell 12. The sample is withdrawn from the gas output 12b of sample cell 12 by pump 44. See FIG. 8. An electrical discharge provided by a high voltage rf oscillation source in analog circuits 22 is applied to cell 12 and cell 13 and creates electrical discharges in the cells. A laser beam from $^{12}CO_2$ laser 16 is passed through the transverse ports of the sample cell 12 and a laser beam from laser 11 is passed along the axis of cell 13. By means of control circuits 28, the laser beams for both lasers 11 and 16 are turned on and off to produce light pulses at particular frequencies. Oscillators in 2 OGE cell Analog circuits 22 are provided with a stabilized low noise current source and a bandpass amplifier. When the laser beam pulses interact with the electrical discharge in the sample cell 12, an electrical change in the discharge, known as an optogalvanic effect, is created which is an indication of the type of gas in the cell. Such a change can be easily determined with high precision and accuracy. In particular, the impedance of the discharge changes, which change is represented by a change in current from the d.c. source driving the rf power. It should be noted that cell 12 is part of and is located in the optical cavity of laser 11. Thus, it can be called an intracavity cell. See FIG. 8. As the laser beam bounces back and forth between the mirrors of the laser cavity, the impact of the beam is repeated multiple time, which greatly improves the sensitivity of the system.

Similarly, $^{14}CO_2$ laser 11 produces a laser beam that is applied to reference cell 13. The circuit 28 causes laser 11 to produce light pulses that are supplied to discharges in the cells. When the laser beam pulses interact with the electrical discharge in the reference cell, a change in the impedance of the cell is created that reflects the OG effect. Such a change can be simply determined with high precision and accuracy by measuring the d.c. driving current for the reference cell. The reference gas is typically a gas highly enriched in $^{14}C$- to a level near 1%. The reference cell allows sensitivity to a few parts per thousand or about 1 part in $10^5$.

As indicated, the sample cell 12 is placed inside the laser cavity of laser 11 where the higher laser power and vastly increased path length due to the reflected (stored) light, amplifies the OGE by $\sim 10^7$, hence allowing detection at the part per trillion level. By carefully taking the ratio of the sample to the reference and averaging for longer times (several minutes), accuracies of a few percent in the measured OGE are obtained. Using a series of reference samples, a calibration curve can be obtained thus allowing the measurement of unknown samples.

A partially reflecting mirror 17 causes light from either laser to enter $CO_2$ spectrum analyzer 19. The analyzer 19 is used for coarse wavelength tuning. The electrical signals from both sample cell 12 and reference cell 13 are applied to analog circuits 22 in the electronics module. These analog signals are converted to digital signals in digital signal processing circuit 24 and are then applied to the software/GUI processing module 30. The module 30 monitors the electrical impedance of the discharge and provides an impedance signal representing the impedance. Since the impedance is varied due to the periodic application of the laser beams to the sample cell, the impedance amplitude is periodically varied at the modulation frequencies that are the pulse rate of the laser beams. Thus, the impedance signal will include a first component varying at a first component frequency, which may be equal to the first modulation frequency or a harmonic thereof and a similar component at a second frequency for the second laser 16.

The software module 30 receives the reference optogalvanic (OG) signal and the sample OG signal in circuit 31. The raw signal is a digitized representation of the analog signal that represents a combined mixture of the optogalvanic signals from both lasers from the Reference Cell and the Sample Cell. Each cell's raw OGE signal is separated into repetitive waveforms based on the modulation frequency of each laser. Each raw waveform is then divided by the fundamental laser frequencies to calculate the data point for wavelets, which represent the coherent averages of the two signals for each cell in circuit 32. Then Fast Fourier Transforms (FFT) are performed in module 33 on the output of circuit 32 yielding 4 averaged signals each second. Module 34 averages the outputs of FFT 33 over 100 or more seconds. The averaged outputs are normalized, and the background is subtracted. The result is compared with standards or with a previously determined calibration curve in modules 35 and 36. The desired ratio $^{14}C/^{12}C$ and $^{12}C$ mass is generated to arrive at a final result. In particular, to determine the amount of a dilute species ($^{14}C$) to dominant species ($^{14}C$) in an analyte.

Figure 2:
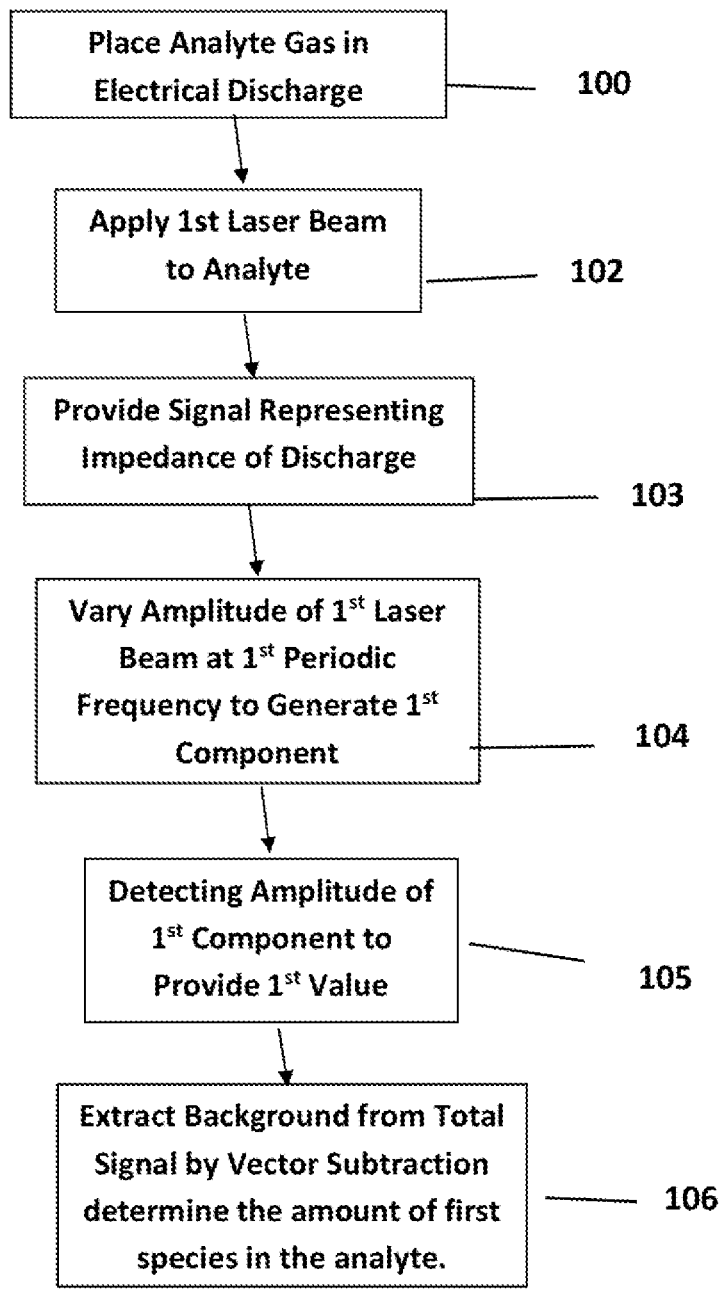
FIG. 2 is a flow chart showing the method of operation of the system of FIG. 1 for determining a first species in an analyte.
Figure 3:
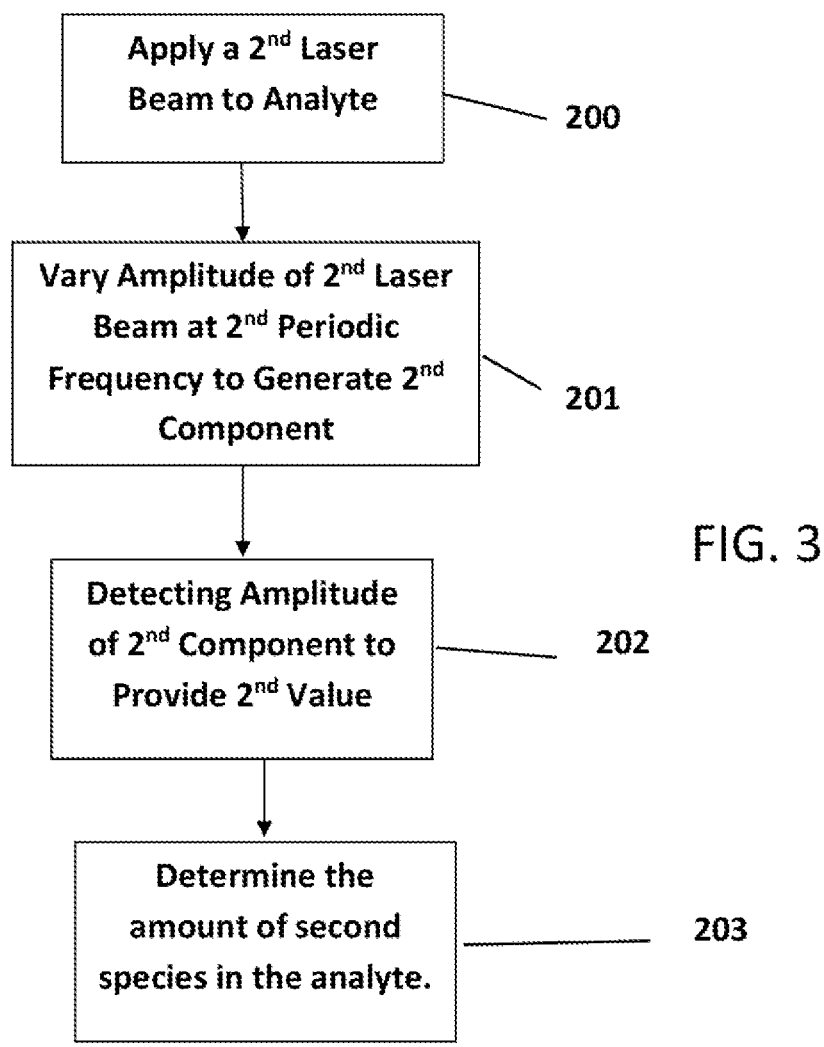
FIG. 3 is an additional flow chart showing the method of operation of the system of FIG. 1 for determining a second species in the analyte.

In operation the system of FIG. 1 operates according to the flow charts of FIG. 2 and FIG. 3. In the first step of the operation (Step 100) the sample or analyte 40 is maintained in gaseous form in the electrical discharge created in sample cell 12. Then a first radiation (e.g., a laser beam from carbon dioxide laser 1I is applied to the analyte in the discharge so that it interacts with a first species in the analyte to produce an optogalvanic effect. (Step 102) A second radiation (laser beam from carbon dioxide laser 11) is applied to the analyte in the discharge (Step 200 in FIG. 3) so that the radiation interacts with a second species in the analyte to produce a second optogalvanic effect. The current flowing through cell 12 is monitored as a way of providing a signal related to the impedance of the discharge. (Step 103) While the current (impedance) signal is being monitored, the laser beams are periodically varied at first and second modulation frequencies generated by the circuit 28. (Steps 104 and 201). As a result, the impedance signal includes a first component varying at a first component frequency which is equal to the first modulation frequency or a harmonic thereof and a second component varying at a second component frequency equal to the second modulation frequency or a harmonic thereof. The analog circuit 22 provides signals representing the impedance variations of the discharge, which via digital analysis in circuits 24, 30 provides the amount of the two species in the sample. (Steps 105 and 202).

The detecting step in FIG. 2 is performed so that the values are substantially independent of the phases of the components relative to the phase of the periodic variation in the amplitude of the laser beams. Then the background is extracted from the total signal by vector subtraction of background components. (Step 106) The background components were previously determined first with a buffer or reference gas sample and second with a $^{14}CO_2$ free sample.

The amount of second species in the analyte is determined from the detection of the amplitude of the $2^{nd}$ component. (Step 203)

Variations of the current can be detected with a pair of correlation signals varying at the first component frequency in quadrature with one another to provide a first real correlated signal and a first imaginary correlated signal. The amplitudes of the correlated signals are determined to provide a first real magnitude and a first imaginary magnitude. The first real magnitude and the first imaginary magnitude are combined to provide the first value. The combining step includes the step of computing the phase as the arctangent of the first imaginary component divided by the first real component The detecting step 105 may also include the steps of sampling the impedance signal at each of a succession of sampling times and providing a sample value for each sampling time in digital form representing the impedance signal at such sampling time and storing the digital sample values in circuit 31. The detecting step may further include the step of digitally averaging sample values over a plurality of cycles of the first component of the impedance signal with circuit 34, so that sample values for times delayed from one another by an integral number of periods of the first component are added to one another, thereby providing a set of averaged sample values representing an averaged cycle of the first component. Each of the averaged sample values is associated with a different time.

The system next provides each correlation signal as a set of correlation signal values in digital form. Each correlation value in the set for one correlation signal being associated with a different time. The step of correlating the first component with each correlation signal includes the step of digitally multiplying each averaged sample value by the correlation value for such correlation signal associated with the same time as such averaged sample value to thereby provide a set of correlated values for each the correlation signal. The step of determining the magnitudes of the correlated signals includes the step of digitally summing the correlated values for each correlated signal.

When first and second species are detected they are multi-atomic species. In particular they have the same chemical composition but include different isotopes of the same element. For example, they may be carbon dioxide moieties including different isotopes such as $^{14}CO_2$, $^{13}CO_2$ and $^{12}CO_2$.

A further extension of the method includes the step of determining a relationship between the amounts of the first and second species in the analyte by comparing the first and second values. This can be achieved by determining a ratio between the first and second values.

The high voltage oscillator for controlling the discharges, the current supply for the oscillator and the band pass amplifier may be any convenient circuit, but preferably are those disclosed in FIGS. 4-7 of the present application.

Figure 4:
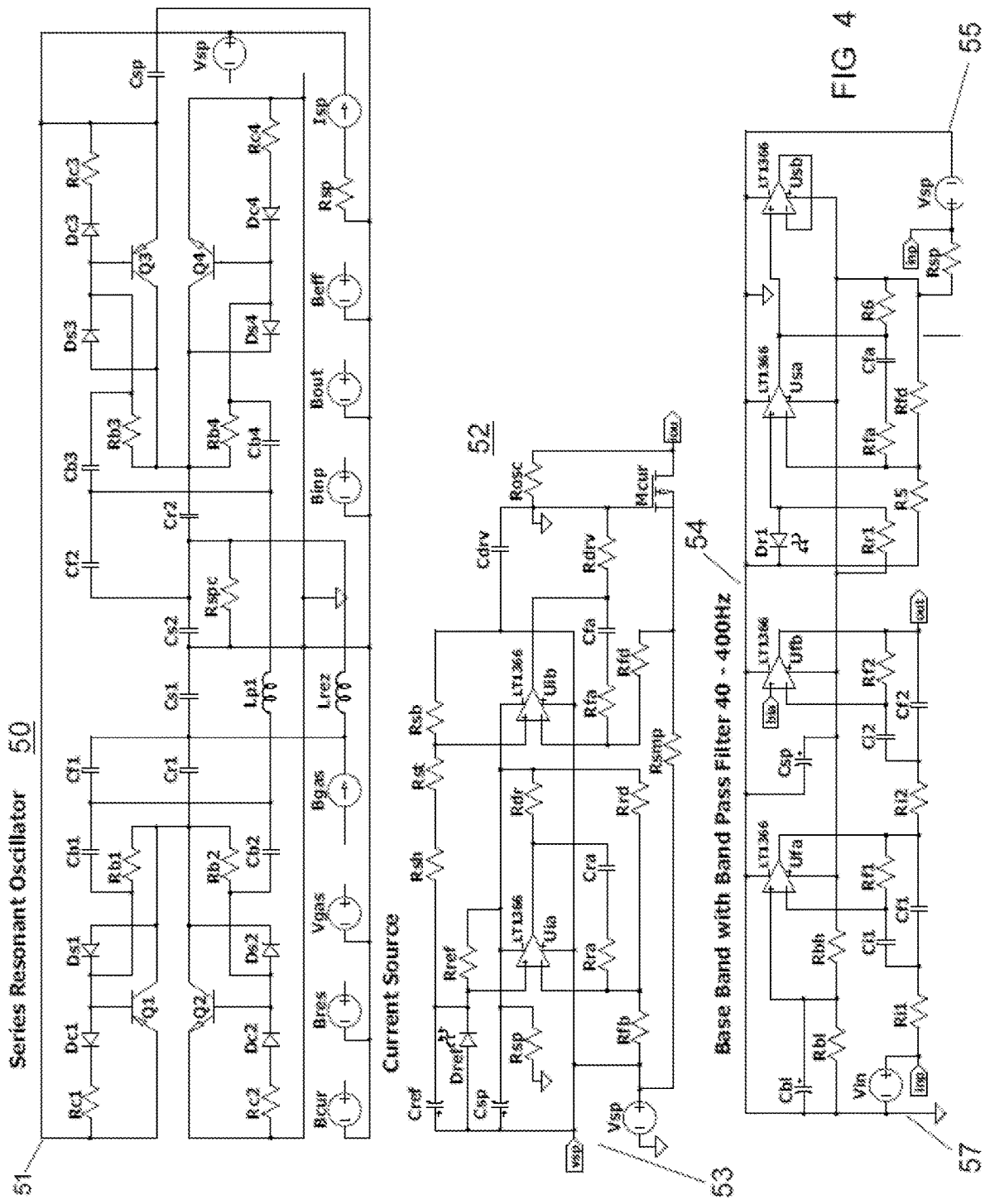
FIG. 4 is a schematic diagram of an oscillator according to one embodiment of the present invention.

FIG. 4 shows a series resonant oscillator according to an illustrative embodiment of the present invention. It includes three parts; a high voltage oscillator section 50, a low noise stable current source section 52 and a band pass amplifier.

The high voltage oscillator section 50, in one or more embodiments, may be part of analog circuit 22. The low noise stable current source section 52 and the band pass amplifier 54, in one or more embodiments, may be parts of the 2 OGE Cell Analog Circuits 22.

The power input for the oscillator is d.c. supply voltage Vps 51, which also can provide the discharge in an OGE system. The supply Vps is generated from raw voltage 53 in current source 52 at output 55. This oscillator circuitry provides unprecedented sensitivity for OGE detection of dilute species, especially rare gases such as $^{14}C$ in ambient $CO_2$ where the concentration is about 1 part per trillion.

The detection of $^{14}CO_2$ requires the use of two OGE systems, one for an unknown sample and a second for a stable reference system, where the reference is highly enriched in $^{14}C$- to a level near 1%. The reference cell allows sensitivity to a few parts per thousand or about 1 part in $10^5$. The sample cell is placed inside a laser cavity where the higher laser power and vastly increased path length amplifies the OGE by ~$10^7$, hence allowing detection at the part per trillion level. By carefully taking the ratio of sample to reference and averaging for longer times (several minutes), accuracies of a few percent in the measured OGE are obtained. Using a series of reference samples, a calibration curve can be obtained thus allowing the measurement of unknown samples.

The current which causes the discharge is from Vsp. Measuring the variation in Vsp provides an indication of the detected species measured by the OGE system. Prior to measurement, the Vsp signal is filtered in base band-pass amplifier 54 where Vsp is applied to an input 57 and the filtered signal is at 59.

Figure 5:
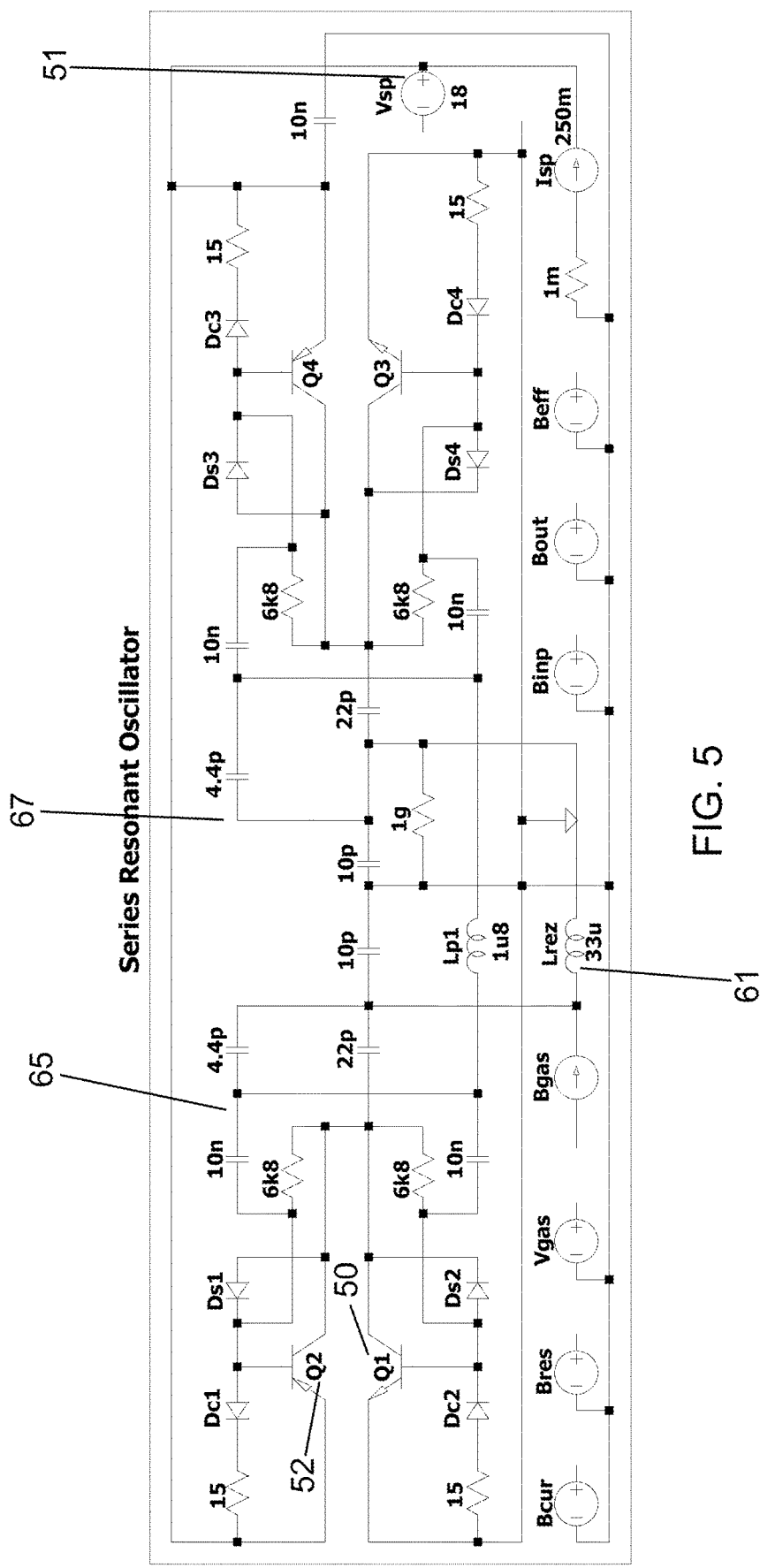
FIG. 5 is an enlarged schematic diagram of the high voltage portion of the oscillator of FIG. 4.

An embodiment of the high voltage oscillator 50, which is shown enlarged in FIG. 5, has 4 transistors in what might be called a series resonant oscillator configuration. Since there is left/right symmetry, only the left side, which is a variation of the parallel resonant Pierce oscillator, needs to be reviewed in detail. In FIG. 5 the two transistors 60, 62 ($Q_{1,2}$) have common emitter complimentary symmetry, thus, they amplify inverted. The collectors feed the series resonant circuit 63 ($C_{r1,2}$, $L_{res}$), where inductor 61 ($L_{res}$) is the main high voltage resonance inductor. At resonance, only resistance is left. Therefore, the current is in phase with the drive voltage from the transistors 60, 62. Hence, the voltage at inductor 61 ($L_{res}$) must lead by 90°.

Feedback capacitors 65, 67 ($C_{f1,r1}$) develop a feedback current that is ultimately applied to the bases of the transistors 60, 62. The current must lead the voltage by 90°. Since the voltage is already leading by 90°, the total is 180° or inversion. This inversion in combination with the amplifier inversion produces non-inversion for total positive feedback or regenerative oscillation.

The oscillation is strong. The transistors 60, 62 of the oscillator operate in class D mode, i.e., either fully on or fully off, with no time spent in the active linear region. When fully on, they contribute negligible noise voltage like a piece of wire. When fully off, they contribute negligible noise current like an open circuit. In this way, the resonance is directly connected to the oscillator power current source.

Since the transistors 60, 62 switch fully between on and off, they spend very little time in the active region. The waveform at their collectors is a square wave. When off, they generate no noise. When fully switched on, their resistance is very low <10 ohms, hence there is negligible noise contribution. The efficiency of the transistors is ~80%. The total efficiency including inductor 61 ($L_{res}$) is ~50%.

Since they are fully switched, the transistors essentially alternately connect the resonance to ground and supply voltage $E_g$. Hence the power supply rail is intimately connected to the resonance. The resistance of the resonance is reflected as the DC resistance of the oscillator at the power supply rail and can be used to monitor the OGE. When used with a current source supply, DC resistance changes will produce supply voltage changes thus, the oscillator is self-demodulating, or feedback stabilized.

The right side of FIG. 5 is a mirror of the left side just explained. The oscillator output is across impedance 63 where the outputs of both sides are combined. This is across vh1, vh2 in FIG. 1.

Figure 6:
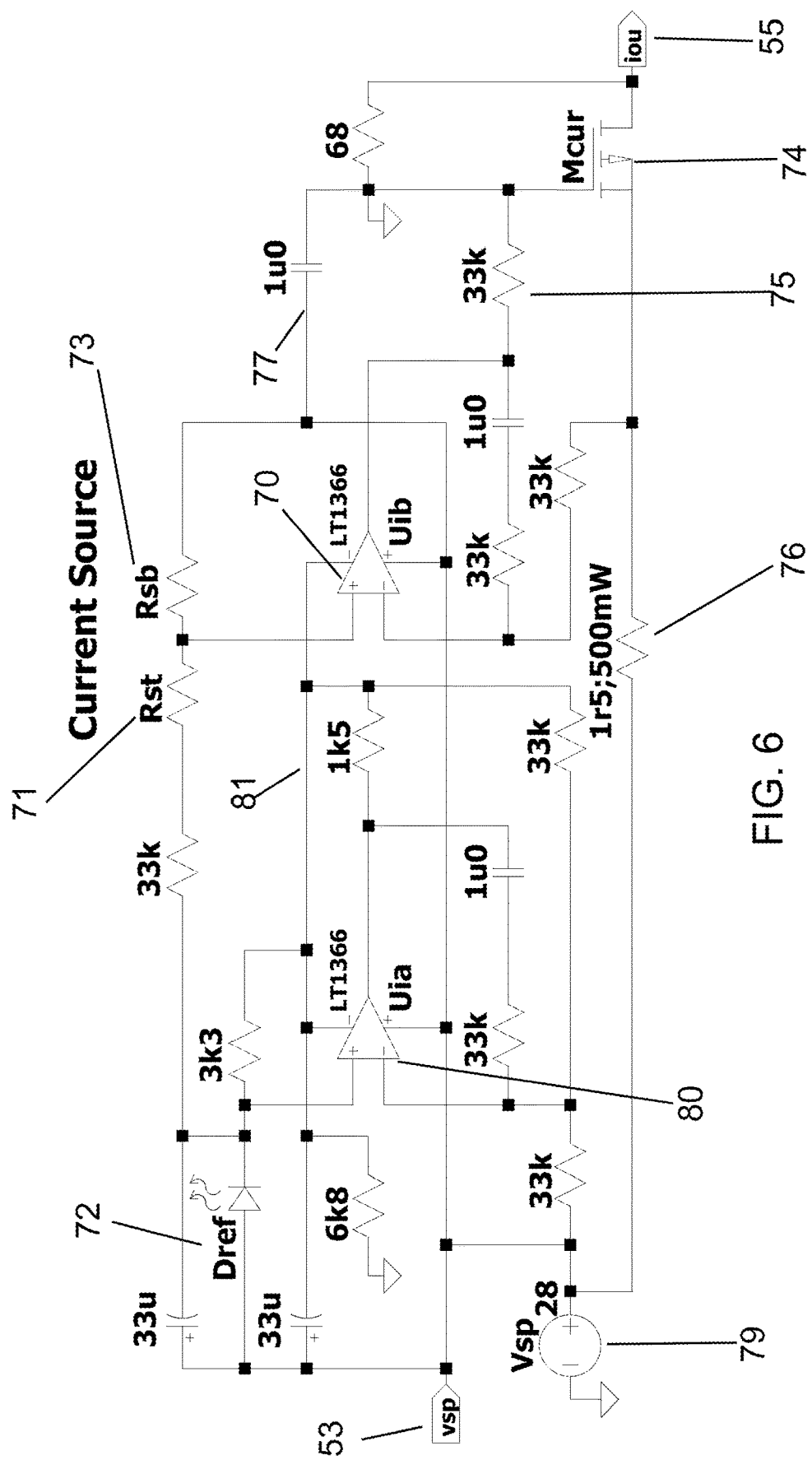
FIG. 6 is an enlarged schematic diagram of the power current source of the oscillator of FIG. 4.

FIG. 6 is an enlarged view of an illustrative embodiment of the power current source 52 of the present invention, which provides current to the high voltage oscillator 50.

The oscillator 50 requires a low noise current source 52 at Vsp 11 to allow for the detection of small load changes. The input raw power to the current power source 52 is at input 53. Operational amplifier 70 ($U_{ib}$) provides the low noise output current at output 55. A forward biased LED 72 ($D_{ref}$) serves as a 3V quiet reference voltage. Resistors 63 73 ($R_{sh}$, $R_t$) form an adjustable voltage divider of the reference voltage that is used to set the constant current fed to the oscillator. Operational amplifier 70 ($U_{ib}$) drives the mosfet transistor 74 ($M_{cur}$) through resistor 75 ($R_{drv}$) and capacitor 77 ($C_{drv}$), which form a low band pass filter with a cutoff of ~5 Hz, greatly reducing the operational amplifier noise contribution. In effect the only noise contribution is from Mosfet transistor 74 ($M_{cur}$). The source of Mosfet 74 is connected back to the 28-volt supply 79 through resistor 76 ($R_{smp}$). The voltage drop across resistor 76 is negative feedback for operational amplifier 70, so that the voltage drop across resistor 76 is equal to the divided voltage reference. As a result, there is a constant current that flows into the source of Mosfet 74. Since transistor 74 is a field effect transistor (FET), its drain current is exactly equal to its source current. The drain current is the supply current for the oscillator and is available at output 55 as Vsp.

Operational amplifier 80 ($U_{ib}$) provides a quiet regulated supply for operational amplifier 70 ($U_{ib}$). Amplifier 80 is a non-inverting amplifier with a gain of 2. It amplifies the reference voltage from diode 72 to produce the regulated power input for amplifier 70 through resistor 81 ($R_{dr}$).

Since the resonant load is directly reflected back to the oscillator power rail (Vsp), the current source allows load variations to manifest as voltage changes. The "current source" is actually a large inductance. It behaves as a voltage source in the long term, establishing the desired operating point, but it behaves as a current source at the desired signal frequencies, allowing the afore mentioned signal to be detected.

Figure 7:
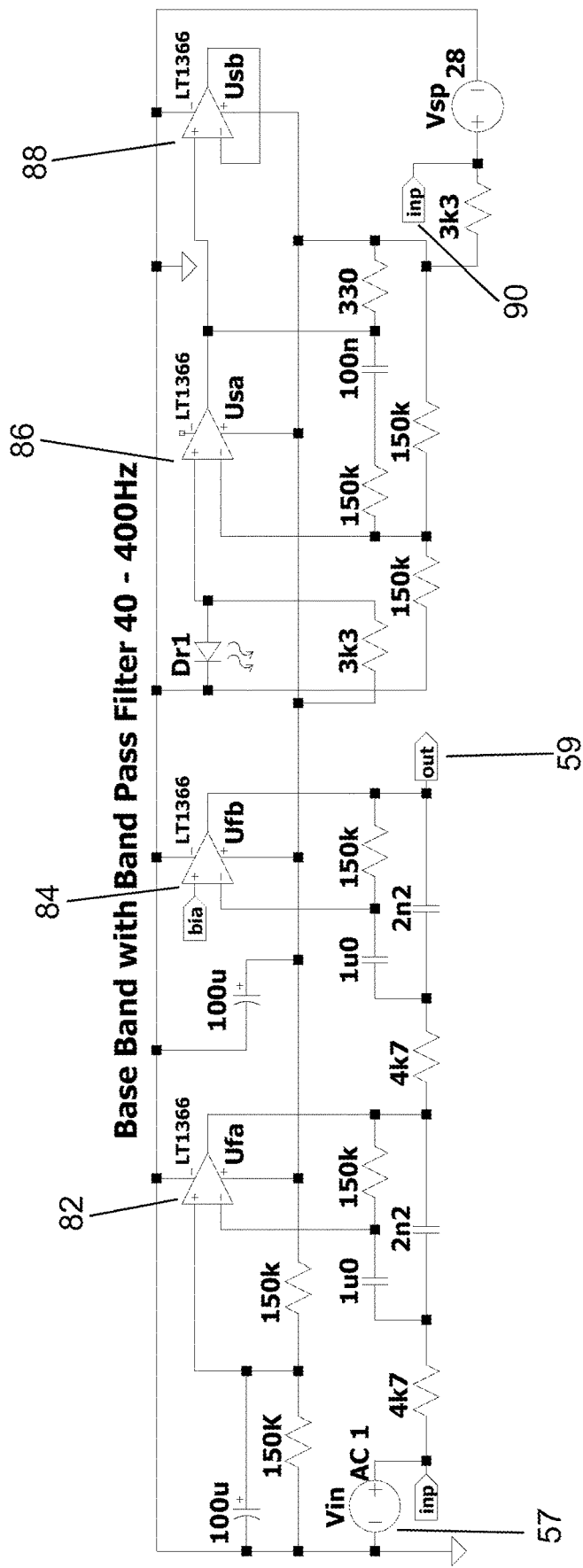
FIG. 7 is an enlarged schematic diagram of the band pass amplifier of the oscillator of FIG. 6.

FIG. 7 is an enlarged view of an illustrative embodiment of the band pass amplifier 54 of the present invention. The demodulated load changing supply voltage Vin 83 is fed to the base band amplifier.

The base band amplifier has two stages, operational amplifiers 82, 84 ($U_{fa,b}$). They are multiple feedback (MFB) band pass amplifiers. They each have a gain of ~32, for a total gain of ~1K. The input Vin 57 is applied to the inverting input of amplifier 82. The output of amplifier 82 is applied to the inverting input of amplifier 84. The output of amplifier 84 is the signal output 89. The circuit passes signals with a band pass frequency between 40 and 400 Hz. It is this signal that is monitored during OGE.

Amplifiers 86, 88 ($U_{sa}$, $U_{sb}$) provide a quiet regulated supply for amplifiers 82, 84 using light emitting diode (LED) 83 ($D_{r1}$) as a voltage reference. Amplifiers 86, 88 are non-inverting amplifiers with a gain of 2. The raw voltage from input 80 is provided to the diode 83 to generate the reference voltage.

While any band pass filter could have been used, the MFB is preferred for its simplicity. In addition, it removes any requirement for CMRR (common mode rejection ratio) of the op amp. Also, MFBs as opposed to Sallen-Key filters have no high frequency feed forward defect.

The above described and shown circuitry allows unprecedented sensitivity for OGE detection of dilute species, especially rare gases such as $^{14}C$ in ambient $CO_2$ where the concentration is about 1 part per trillion.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

We claim:

1. A method of determining the composition of an analyte including the steps of:
   (a) maintaining the analyte in gaseous form in an optical cavity;
   (b) applying a stable high voltage oscillating signal to the optical cavity to produce a discharge in the optical cavity;
   (c) applying a first radiation from a radiation cavity to said analyte in said discharge so that said radiation interacts with a first species in said analyte to produce an optogalvanic effect that results in a change in the electrical impedance of the optical cavity, said optical cavity being located in said radiation cavity;
   (d) monitoring the electrical impedance of said discharge and providing an impedance signal representing said impedance;
   (e) periodically varying the amplitude of said first radiation at a first modulation frequency, whereby said impedance signal will include a first component varying at a first component frequency equal to the first modulation frequency or a harmonic thereof;
   (f) detecting the amplitude and phase of said first component to provide a first value representing said amplitude and phase of said first component, whereby said first value represents the amount of said first species in said analyte, said detecting step being performed so that said phase value is relative to the phase of said periodic variation in amplitude of said first radiation; and (g) extracting a background from the total signal by vector subtraction of background components previously determined with first a buffer gas sample and secondly a first analyte free sample.

2. The method as claimed in claim 1 wherein the step of extracting a background involves the steps of:
maintaining a reference gas in a reference cell:
applying the first radiation to the reference gas in said reference cell;
applying the oscillation signal is to the reference cell to create an electrical discharge inside of the reference cell;
monitoring a second current representative of the electrical impedance of the discharge in the reference cell and providing an impedance signal representing said background.

3. The method as claimed in claim 1 wherein the maintenance of the analyte in gaseous form in the electrical discharge is carried out by a series resonant oscillator configuration driven by a stabilized current source, and further including the steps of:
detecting variations of the current with a pair of correlation signals varying at said first component frequency in quadrature with one another to thereby provide a first real correlated signal and a first imaginary correlated signal, and
determining the amplitudes of said correlated signals to provide a first real magnitude and a first imaginary magnitude and combining said first real magnitude and said first imaginary magnitude to provide said first amplitude value.

4. A method as claimed in claim 3 wherein said combining step includes the step of computing the phase as the arctangent of first imaginary component divided by the first real component.

5. A method as claimed in claim 3 wherein said detecting step includes the steps of sampling said impedance signal at each of a succession of sampling times and providing a sample value for each said sampling time in digital form representing the impedance signal at such sampling time and storing said digital sample values.

6. A method as claimed in claim 5 wherein said detecting step further includes the step of digitally averaging sample values over a plurality of cycles of said first component of said impedance signal so that sample values for times delayed from one another by an integral number of periods of said first component are added to one another to thereby provide a set of averaged sample values representing an averaged cycle of said first component, each of said sets of averaged sample values being associated with a different time.

7. A method as claimed in claim 6 further comprising the step of providing each said correlation signal as a set of correlation signal values in digital form, each said correlation value in the set for one said correlation signal being associated with a different time, the step of correlating said first component with each said correlation signal including the step of digitally multiplying each said averaged sample value by the correlation value for such correlation signal associated with the same time as such averaged sample value to thereby provide a set of correlated values for each said correlation signal.

8. A method as claimed in claim 7 wherein said step of determining the values of said correlated signals includes the step of digitally summing the correlated values for each said correlated signal.

9. A method as claimed in claim 1 wherein said first component frequency is equal to said first modulation frequency.

10. A method as claimed in claim 1 further comprising the steps of:
(a) applying second radiation to said analyte in said discharge so that said radiation interacts with a second species in said analyte to produce an optogalvanic effect;
(b) periodically varying the amplitude of said second radiation at a second modulation frequency, whereby said impedance signal will include a second component varying at a second component frequency equal to said second modulation frequency or a harmonic thereof; and
(c) detecting the amplitude of said second component to provide a second value representing said amplitude of said second component, whereby said second value represents the amount of said second species in said analyte, said detecting step being performed so that said second value is substantially independent of the phase of said second component relative to the phase of said periodic variation in amplitude of said second radiation.

11. A method as claimed in claim 10 wherein said first and second species are multi-atomic species.

12. A method as claimed in claim 11 wherein said first and second species have the same chemical composition but include different isotopes of the same element.

13. A method as claimed in claim 10 wherein said first and second species are carbon dioxide moieties including different isotopes.

14. A method as claimed in claim 10 wherein said first and second species are $^{14}CO_2$ and $^{12}CO_2$.

15. A method as claimed in claim 13 wherein said steps of providing said first and second radiation are performed by operating one or more carbon dioxide lasers or other lasers resonant with specific carbon dioxide molecule resonances.

16. A method as claimed in claim 10 further comprising the step of determining a relationship between amounts of said first and second species in said analyte by comparing said first and second values.

17. A method as claimed in claim 16 wherein said step of determining a relationship includes the step of determining a ratio between said first and second values.

18. A method as claimed in claim 10 further including the steps of:
converting deconvoluted time dependent signals via Fourier transformation into a set of amplitude and phase vectors; and
extracting the non-resonant vector background from the total signal by vector subtraction of background components previously determined with first a buffer gas sample and secondly a rare isotope free sample.

19. A method as claimed in claim 1 further including the steps of
determining the concentration of the resonant species by means of a calibration curve developed with a series of standards;
extracting a measured analyte signal by vector subtraction of a premeasured buffer gas signal vector;
subtracting a premeasured sample with zero concentration of the desired analyte; and normalizing the resultant vector amplitude to the analyte concentration as determined for an abundant isotope.

\* \* \* \* \*